United States Patent [19]

Calvani et al.

[11] Patent Number: 4,751,242

[45] Date of Patent: Jun. 14, 1988

[54] USE OF ACETYL L-CARNITINE IN THE THERAPEUTICAL TREATMENT OF PERIPHERAL NEUROPATHIES

[75] Inventors: Menotti Calvani; Luigi Mosconi, both of Rome, Italy

[73] Assignee: Sigma-Tau Industrie Farmaceutiche Riunite S.p.A., Rome, Italy

[21] Appl. No.: 78,152

[22] Filed: Jul. 27, 1987

[30] Foreign Application Priority Data

Aug. 4, 1986 [IT] Italy .............................. 48358 A/86

[51] Int. Cl.⁴ .......................................... A61K 31/205
[52] U.S. Cl. .................................... 514/554; 514/555; 514/556
[58] Field of Search ........................ 514/554, 555, 556

Primary Examiner—Stanley J. Friedman
Attorney, Agent, or Firm—Ladas & Parry

[57] ABSTRACT

Oral or parenteral administration of 1,000–2,000 mg/day of acetyl L-carnitine or an equivalent amount of a pharmacologically acceptable salt thereof to patients affected by acute or chronic peripheral neuropathy dramatically improves their symptomatological pattern.

8 Claims, No Drawings

USE OF ACETYL L-CARNITINE IN THE THERAPEUTICAL TREATMENT OF PERIPHERAL NEUROPATHIES

DESCRIPTION

The present invention relates to a novel therapeutical utilization of acetyl L-carnitine and its pharmacologically acceptable salts for the therapeutical treatment of peripheral neuropathies.

Previous therapeutical uses of acetyl L-carnitine are already known. For instance, the U.S. Pat. No. 4,194,006, discloses the use of acetyl carnitine in the therapeutical treatment of myocardial arrhythmias and ischemias. The U.S. Pat. No. 4,343,816 discloses the use of acetyl carnitine in the therapeutical treatment of functional peripheral vascular diseases of arteries, such as Reynaud's disease and acrocyanosis. The U.S. Pat. No. 4,346,107 discloses the therapeutical effectiveness of acetyl carnitine in the treatment of patients suffering from impaired cerebral metabolism as it occurs in senile and pre-senile dementia and Alzheimer's disease. There is no relationship at all, however, between the already known therapeutical utilizations of acetyl L-carnitine and the novel utilization which is the subject matter of the present invention.

This will appear more evident from the description which follows wherein a tentative biochemical explanation of acetyl L-carnitine effectiveness in peripheral neuropathies is illustrated.

The definition of peripheral neuropathies is applied to a group of persistent disturbances of the motor neurons of the brain stem and spinal cord and/or the primary sensory neurons and/or the peripheral autonomic neurons, with involvement of the peripheral axons and their attendant supporting structures.

Clinically, these diseases become manifest by impairment of the motor function (atrophy and muscular weakness, loss of tendon reflexes), sensory disturbances (sensation of crawling—formication—and intense cold to the skin, burning or knifelike pains, appearance of dysesthesia or anesthesia zones, etc.), autonomic system disorder (loss of sweating, irregular pupils, altered salivation and lacrimation), or by a combination of the foregoing.

With regard to their etiology, peripheral neuropathies constitute a heterogeneous class of diseases because their etiology may be secondary to viral infections (herpes zoster), schaemia (arteriosclerosis), metabolic unbalances (diabetes, renal and liver insufficiency), drug-induced toxicity (adriamicine, isoniazide, nitrofurantoin), mechanical stresses (compression, entrapment, fracture or dislocation of bones), radiations, genetic factors and pathologies of the immune system.

However, no matter what the actual etiological cause of the disease form is, it is always possible to detect an alteration in the membrane fluidity resulting from an alteration of the cell lipids, cholesterol and gangliosides.

Lipids play a very important role in defining the tertiary and quaternary protein structure and in maintaining the stability of adenosintriphosphatase structure. In fact, their absence brings about the enzyme inactivity.

It has now been found that, surprisingly, the use of acetyl L-carnitine and its pharmacologically acceptable salts is effective in the therapeutical treatment of peripheral neuropathies.

Therefore, the present invention realtes to the use of acetyl L-carnitine and its pharmacologically acceptable salts for producing a pharmaceutical composition for the therapeutical treatment of peripheral neuropathies. In practice, from about 1,000 to about 2,000 mg of acetyl L-carnitine or an equivalent amount of a pharmacologically acceptable salt thereof are administered daily via the oral or parenteral route. Generally, the treatment is continued for about 30–60 days.

It is apparent that in the light of the therapeutical use of the present invention the most suitable pharmaceutical compositions are those compositions which in unit dosage form comprise from about 500 to about 1,000 mg of acetyl L-carnitine or an equivalent amount of a pharmacologically acceptable salt thereof and a pharmacologically acceptable excipient thereof.

Examples of suitable compositions in unit dosage form are for instance disclosed in the U.S. Pat. No. 4,464,393.

The effectiveness of acetyl L-carnitine in treating peripheral neuropathies has been corroborated both with pharmacological tests in an experiment animal model and with clinical trials. Some of these tests are illustrated hereinbelow.

PHARMACOLOGICAL TESTS

Clinical Evaluation of Functional Restoration Following Cutting and Immediate Microsurgical Reconstruction of the Sciatic Nerve in Rats In this test male Wistar rats weighing 200–250 grams were used. Following general anesthesia (Nembutal, 4 mg/100 g e.p.) the sciatic nerve was aseptically isolated at the thigh bilaterally. The nerve was incised just distally to the branch to the gluteus maximus and immediately reconstructed via microsurgical peri-perineural anastomosis. Following surgery the rats were randomly subdivided into four groups and subcutaneously injected according to the following scheme:

| Experimental group | Number of rats | Drug | Dose/day |
|---|---|---|---|
| I | 5 | Saline | 0.2 ml |
| II | 5 | L-carnitine | 50 mg/kg |
| III | 5 | Acetyl L-carnitine | 50 mg/kg |
| IV | 5 | Gangliosides | 50 mg/kg |

The treatment began on the first day one minute following surgery and was continued for eight weeks. After this time period, the degree of functional restoration was evaluated according to the following scale proposed by Richardson et al, "Percussive injury to peripheral nerve in rats", J. Neurosurg. 51, 178–187 (1979), and Zalewsk et al, "An evaluation of nerve repair with nerve allografts in normal and immunologically tolerant rats", J. Neurosurg. 52, 557–563 (1980):

| | |
|---|---|
| 0 | Atrophy of the anterior tibial muscle (AT) and toe long extensor (TLE), foot drop |
| 1 | No atrophy of AT and TLE, foot drop |
| 2 | No atrophy of AT and TLE, no foot drop |
| 3 | No atrophy of AT and TLE, restoration of foot dorsal flexion |
| 4 | No atrophy of AT and TLE, spreading out of toes. |

RESULTS

The degree of functional restoration is reported in the following table:

| Experimental group | Clinical rating |
| --- | --- |
| I | 2.2 ± 1.0 |
| II | 2.8 ± 1.1 |
| III | 3.3 ± 0.7 |
| IV | 1.1 ± 1.1 |

The clinical rating is significantly higher in the group III rats treated with acetyl L-carnitine with respect to the controls treated with placebo ($p \leq 0.05$).

CLINICAL TRIALS 27 patients affected by acute or chronic peripheral neuropathy were admitted to the trial. Of these patients, 6 had diabetic polyneuropathy, 9 had post-herpetic neuropathy, 4 had radiation neuropathy, 5 had deafferentation neuropathy (causalgia, phantom limb syndrome) and 3 had traumatic neuropathy.

The objective and subjective clinical symptoms of the patients were obviously polymorphic depending on the specific etiological cause of the neuropathy. However, pain, the presence of cutaneous areas presenting dysesthesia and impairment of the motor function were present in all the subjects, although with varying degrees of intensity. Consequently, with a view to evaluating the treatment effectiveness, the symptoms DYSESTHESIA, IMPAIRMENT OF MOTOR FUNCTION and PAIN were considered.

The zones of dysesthesia (hyper, hypo and anesthesia) were located, numbered and their surface area was measured. Their overall surface area was taken equal to 100 and indicated in table 1 by the symbol +++, for each patient.

The impairment of motor function, lacking at the moment any electromyographical evaluation, which would be the optimum, was clinically evaluated and the value reached by every patient was taken equal to 100 and indicated in table 2 with +++.

With regard to the symptoms DYSESTHESIA and IMPAIRMENT OF THE MOTOR FUNCTION, each patient was regarded as inner control of himself (or herself) and consequently the pathology level before treatment was in each case taken equal to 100 (+++), even though the actual level varied from patient to patient.

The measured value, which is shown in the tables, is therefore the percentage amount of symptom abatement.

PAIN was on the other hand evaluated by using the Keele-Dundee scale in combination with the visual scale of Scott-Huskisson.

It should be however noted that the data relating to modulation of the pain symptoms are reported for completeness sake since the results obtained can not be ascribable to the acetyl L-carnitine action exclusively, since some of the patients have been currently treated with analgesics.

Observations were carried out before treatment began and after 15, 30 and 45 days of therapy.

All the patients were orally administrated 1,000–2,000 mg/day of acetyl L-carnitine, as the only neurotrophic drug, for periods varying from 30 to 45 days.

Of the treated patients, 13 had never received any previous treatment, whereas 14 had previously been treated with citicoline and neuramide without deriving appreciate benefits.

RESULTS

(1) DYSESTHESIA

It was shown that the surface area of dysesthesia and anesthesia zones was decreased by one-third in 13/27 patients, decreased by two-thirds in 11/27 patients and unchanged in 3/27 patients, upon evaluation made on the fifteenth day.

When checked on the thirtieth day, 6/27 patients showed a decrease of at least one-third, 14/27 showed a decrease of at least two-thirds and 7/27 showed complete remission of symptoms.

When checked on the fortyfifth day, it was observed that only one patient was a non-responder, whereas 26 patients were responders. Of these, 12/26 patients showed complete clinical remission (see table 1).

TABLE 1

| SYMPTOM: DYSESTHESIA | | | | |
| --- | --- | --- | --- | --- |
| | 00 | 15 | 30 | 45 |
| POST-HERPETIC NEUROPATHY | +++ | ++ | ++ | + |
| POST-HERPETIC NEUROPATHY | +++ | ++ | + | -- |
| POST-HERPETIC NEUROPATHY | +++ | +++ | ++ | + |
| POST-HERPETIC NEUROPATHY | +++ | ++ | + | -- |
| POST-HERPETIC NEUROPATHY | +++ | ++ | ++ | ++ |
| POST-HERPETIC NEUROPATHY | +++ | + | -- | -- |
| POST-HERPETIC NEUROPATHY | +++ | + | -- | -- |
| POST-HERPETIC NEUROPATHY | +++ | ++ | + | + |
| POST-HERPETIC NEUROPATHY | +++ | + | + | -- |
| DIABETIC POLYNEUROPATHY | +++ | ++ | + | + |
| DIABETIC POLYNEUROPATHY | +++ | + | + | + |
| DIABETIC POLYNEUROPATHY | +++ | + | -- | -- |
| DIABETIC POLYNEUROPATHY | +++ | ++ | + | + |
| DIABETIC POLYNEUROPATHY | +++ | + | + | + |
| DIABETIC POLYNEUROPATHY | +++ | + | -- | -- |
| DEAFFERENTATION NEUROPATHY | +++ | ++ | + | -- |
| DEAFFERENTATION NEUROPATHY | +++ | ++ | + | + |
| DEAFFERENTATION NEUROPATHY | +++ | +++ | ++ | + |
| DEAFFERENTATION NEUROPATHY | +++ | ++ | ++ | + |
| DEAFFERENTATION NEUROPATHY | +++ | +++ | ++ | + |
| TRAUMATIC NEUROPATHY | +++ | + | + | -- |
| TRAUMATIC NEUROPATHY | +++ | + | -- | -- |
| TRAUMATIC NEUROPATHY | +++ | + | -- | -- |
| RADIATION NEUROPATHY | +++ | + | -- | -- |
| RADIATION NEUROPATHY | +++ | ++ | + | + |
| RADIATION NEUROPATHY | +++ | ++ | + | + |
| RADIATION NEUROPATHY | +++ | ++ | + | + |

(2) IMPAIRMENT OF MOTOR FUNCTION

Upon evaluation carried out on the fifteenth day, the degree of motor function impairment appeared to be reduced by one-third in 12/27 patients, and by two-thirds in 11/27 patients. Lastly, 4/27 patients showed complete remission of motor function impairment. When checked on the thirtieth day, 3/27 patients showed a decrease of at least one-third, 16/27 showed a decrease of at least two-thirds and 8/27 showed complete remission of symptoms.

The check carried out on the fortyfifth day showed that only one patient was a non-responder whereas 26 patients were responders. Of these, 12/26 patients showed complete clinical remission (see table 2).

TABLE 2

| SYMPTOM: IMPAIRMENT OF MOTOR FUNCTION | | | | |
|---|---|---|---|---|
| | 00 | 15 | 30 | 45 |
| POST-HERPETIC NEUROPATHY | +++ | + | + | -- |
| POST-HERPETIC NEUROPATHY | +++ | -- | -- | -- |
| POST-HERPETIC NEUROPATHY | +++ | ++ | + | + |
| POST-HERPETIC NEUROPATHY | +++ | -- | -- | -- |
| POST-HERPETIC NEUROPATHY | +++ | + | + | -- |
| POST-HERPETIC NEUROPATHY | +++ | ++ | + | + |
| POST-HERPETIC NEUROPATHY | +++ | -- | -- | -- |
| POST-HERPETIC NEUROPATHY | +++ | ++ | + | + |
| POST-HERPETIC NEUROPATHY | +++ | + | + | -- |
| DIABETIC POLYNEUROPATHY | +++ | ++ | + | + |
| DIABETIC POLYNEUROPATHY | +++ | ++ | + | + |
| DIABETIC POLYNEUROPATHY | +++ | + | -- | -- |
| DIABETIC POLYNEUROPATHY | +++ | ++ | + | + |
| DIABETIC POLYNEUROPATHY | +++ | + | + | + |
| DIABETIC POLYNEUROPATHY | +++ | + | + | + |
| DEAFFERENTATION NEUROPATHY | +++ | ++ | + | -- |
| DEAFFERENTATION NEUROPATHY | +++ | ++ | ++ | + |
| DEAFFERENTATION NEUROPATHY | +++ | ++ | ++ | ++ |
| DEAFFERENTATION NEUROPATHY | +++ | + | + | + |
| DEAFFERENTATION NEUROPATHY | +++ | ++ | ++ | + |
| TRAUMATIC NEUROPATHY | +++ | + | -- | -- |
| TRAUMATIC NEUROPATHY | +++ | + | -- | -- |
| TRAUMATIC NEUROPATHY | +++ | -- | -- | -- |
| RADIATION NEUROPATHY | +++ | + | -- | -- |
| RADIATION NEUROPATHY | +++ | + | + | + |
| RADIATION NEUROPATHY | +++ | ++ | + | + |
| RADIATION NEUROPATHY | +++ | ++ | + | + |

(3) PAIN

With regard to this symptom, i.e. PAIN, before treatment began, 13/27 patients were complaining of pain of intensity 5, 7/27 of pain of intensity 4, 3/27 of pain of intensity 3 and 4/27 of pain having intensity comprised between 2 and 1.

Fifteen days following beginning of treatment, the intensity of the pain symptoms subsided in all patients and, in fact, no patient was complaining of pain of intensity 5, 2/27 patients reported pain of intensity 4, 9/27 reported pain of intensity 3 and as many as 14/27 patients reported pain of intensity 1 to 2, whereas 2/27 patients did not complain of any pain.

Thirty days following beginning of treatment, 12/27 patients reported no pain at all, whereas the remaining 15/27 were complaining of pain having intensity 1 to 2.

Fortyfive days following beginning of treatment, the response appeared to be stabilized, 15/27 patients reporting no pain and 12/27 reporting pain comprised between 1 and 2.

The chronologic development of the pain symptoms is shown in table 3.

TABLE 3

| | SYMPTOM: PAIN | | | |
|---|---|---|---|---|
| | 00 | 15 | 30 | 45 |
| 5/4 | 20 | 02 | 00 | 00 |
| 3 | 03 | 09 | 00 | 00 |
| 2/1 | 04 | 14 | 15 | 12 |
| 0 | 00 | 02 | 12 | 15 |

In conclusion, all patients derived benefit from the treatment.

The first improvement indications were detected in the subjective symptoms: in fact, both pain and the sensations of crawling and cold to the skin subsided; subsequently, the dysesthesia and anesthesia zones decreased.

In the patients affected by deafferentation, cutaneous anhydration, which was present in all treated subjects, subsided remarkably.

In the patients affected by post-herpetic neuropathy, an improvement in the impairment of the motor function was noted in the early phase of the treatment, whereas the previously utilized neurotrophic therapies had not brought about any successful result.

The patients affected by traumatic pathologies derived more benefit from acetyl L-carnitine administration than any other patient.

In fact, after only fifteen days of treatment, the motor activity improved considerably, the sensibility to pin pricks and light tapping as well as the ability to discriminate between thermal and tactile sensations were restored.

Also the patients affected by radiation neuropathy improved appreciably.

It is not intended, nor is it necessary, to be bound to any theoretical interpretation in order to justify the therapeutical effectiveness of acetyl L-carnitine in peripheral neuropathies, particularly in post-traumatic neuropathies. It can be postulated, however, that acetyl L-carnitine is likely to perform a "scavenger" effect on the free radicals (superoxide, hydroperoxide) that form in conditions of irregular or insufficient perfusion or during phlogistic processes because of the decreased activity of cytochrome oxidase that controls the metabolic shift between the tetravalent and the bivalent anaerobic route.

Acetyl L-carnitine, by increasing the levels of reduced glutathione, one of the most important antioxidant metabolites, and probably the levels of the cytochrome oxidases, might bring about the free radicals scavenge and the restoration of the tetravalent oxidoreductant respiratory mechanism in general and of the neurons in particular. Moreover, acetyl L-carnitine would affect the neurons by bringing about an increase in ATP-ase and AChE, that are indispensable for optimum neurotransmission.

What is claimed is:

1. A method for treating a patient with a peripheral neuropathy comprising administering to the patient an effective amount of a composition comprising acetyl L-carnitine or an equivalent amount of a pharmaceutically acceptable salt thereof and a pharmaceutically acceptable carrier.

2. A method as in claim 1 wherein the effective amount comprises 1000-2000 mg of acetyl-L-carnitine daily.

3. A method, as in claim 2 wherein the acetyl-L-carnitine is administered for 30-60 days.

4. A method as in claim 1 wherein the composition is administered orally.

5. A method, as in claim 2 wherein the composition is administered parenterally.

6. A method, as in claim 1 wherein the peripheral neuropathy comprises one of the group consisting of post-herpetic neuropathy, diabetic polyneuropathy, deafferentation neuropathy, traumatic neuropathy, and radiation neuropathy.

7. A method, as in claim 1 wherein the peripheral neuropathy is one which is manifested by an alteration in membrane fluidity.

8. A method, as in claim 1 wherein the peripheral neuropathy is secondary to a viral infection, schaemia, metabolic imbalance, drug induced toxicity mechanical stress radiation, genetic factors and pathology of the immune system.

* * * * *